United States Patent [19]

Cupferman et al.

[11] Patent Number: 6,040,347
[45] Date of Patent: Mar. 21, 2000

[54] TREATMENT OF SEBORRHOEA/ CUTANEOUS DISORDERS WITH OCTOXYGLYCEROL

[75] Inventors: Sylvie Cupferman, Paris; Jean-Pierre Laugier, Antony, both of France

[73] Assignee: Societe L'Oreal S.A., Paris, France

[21] Appl. No.: 09/101,623

[22] PCT Filed: Nov. 13, 1997

[86] PCT No.: PCT/FR97/02039

§ 371 Date: Aug. 4, 1998

§ 102(e) Date: Aug. 4, 1998

[87] PCT Pub. No.: WO98/22081

PCT Pub. Date: May 28, 1998

[30] Foreign Application Priority Data

Nov. 15, 1996 [FR] France ................................. 96 13980

[51] Int. Cl.[7] .................................................. A61K 31/08
[52] U.S. Cl. ............................................................ 514/723
[58] Field of Search ............................................... 514/723

[56] References Cited

FOREIGN PATENT DOCUMENTS

| 0 025 302 | 3/1981 | European Pat. Off. . |
| 41 40 474 | 6/1993 | Germany . |
| 93 25208 | 12/1993 | WIPO . |

OTHER PUBLICATIONS

Database WPI, Week 8108, Derwent Publications Ltd., London, GB; AN 81–1255ld, XP002036883, "Stable aq. powder dispersion cosmetic–obtd. by dispersing powder in gel obtd, by addn. of sucrose fatty acid ester, alpha monoglycerineether and surfactant to water", Dec. 13, 1980.

*Primary Examiner*—Rebecca Cook
*Attorney, Agent, or Firm*—Burns, Doane, Swecker & Mathis, L.L.P.

[57] ABSTRACT

The subject-matter of the present invention is the use of octoxyglycerol in a cosmetic or dermatological composition for treating seborrhoea and/or cutaneous disorders which are associated with it, in particular acne and/or greasy skin with a tendency towards acne and/or hyperseborrhoea.

39 Claims, No Drawings

TREATMENT OF SEBORRHOEA/CUTANEOUS DISORDERS WITH OCTOXYGLYCEROL

This is 371 of PCT/FR97/02039 filed Nov. 13, 1997.

The subject-matter of the present invention is the use of octoxyglycerol in a cosmetic or dermatological composition for treating seborrhoea and cutaneous disorders which are associated with it, in particular acne and/or hyperseborrhoea.

The secretion of sebum is a normal phenomenon and useful to the skin and the hair. However, the hypersecretion of sebum, known as seborrhoea, is annoying and sometimes results in a cutaneous pathology, in particular a greasy skin and even one suffering from acne, and a seborrhoeic condition of the scalp. The consequences of the sebaceous hypersecretion and the disturbance of the keratinization of the pilo-sebaceous follicle is that the pilo-sebaceous follicle becomes blocked and that retentional lesions or comedones are formed.

These pathologies and in particular acne and/or hyperseborrhoea relate in particular to the colonization of the skin or hair follicle by microorganisms of the genus Propionibacterium, such as *Propionibacterium acnes*, *Propionibacterium granulosum* or *Propionibacterium avidum*.

These undesirable microorganisms metabolize sebum triglycerides, with the release of the irritant fatty acids responsible for the inflammation which appears during these pathologies.

Use is commonly made, in combating these pathogenic agents, of active agents such as triclosan, hexamidine, hexetidine and benzalkonium chloride. However, the use of these active agents is not without side effects. Thus, triclosan exhibits a not insignificant toxicity, even by the topical route. In addition, it has proved to be insufficiently effective, in particular in certain vehicles where its activity is inhibited by the surfactants. Hexamidine and hexetidine, in the form of salts, are sensitizing substances capable of causing allergies. Furthermore, benzalkonium chloride can prove to be irritating at the normal doses of use. Moreover it destabilizes compositions containing anionic surfactants.

It is thus found that the need remains for topical active agents which have an effect on the pathologies related to microorganisms of the genus Propionibacterium and which have an action at least as effective as the compounds of the prior art, while not exhibiting the disadvantages of the known compounds.

The subject-matter of the present invention is precisely the use of specific compounds which make it possible to obtain this effect.

The Applicant Company has discovered that octoxyglycerol exhibited high activity with respect to *Propionibacterium acnes* and *Propionibacterium granulosum* and could thus be used in a cosmetic or dermatological composition as anti-seborrhoeic and anti-acne active agent.

The document DE-A-4,140,474 certainly describes the use of monoalkyl ethers of glycerol in compositions for cleansing and caring for the skin. However, these compounds are used as supergreasing additives which prevent the drying of the skin in alcohol-based antiseptic and disinfectant compositions, the monoalkyl ethers of glycerol reinforcing the antiseptic effect of the alcohol while preventing the drying of the skin. The use of monoalkyl ethers of glycerol, particularly of octoxyglycerol, to act against pathologies related to *Propionibacterium acnes* and *Propionibacterium granulosum*, and in particular to treat seborrhoea and acne, has never been described.

The document WO 93/25208 describes the use of monoalkyl ethers of glycerol in cytocidal, antibacterial and spermicidal compositions. This document does not specifically describe the activity of the monoalkyl ethers with respect to microorganisms of the genus Propionibacterium and still less pathologies related to *Propionibacterium acnes* and *Propionibacterium granulosum* and in particular seborrhoea and acne. Moreover, octoxyglycerol is not cited in this document.

The subject-matter of the present invention is thus the use of octoxyglycerol in a cosmetic composition for treating seborrhoea of the skin and/or of the scalp and/or cutaneous disorders associated with seborrhoea.

Another subject-matter of the present invention is the use of octoxyglycerol in the manufacture of a medicament intended to treat seborrhoea of the skin and/or of the scalp and/or cutaneous disorders associated with seborrhoea.

The cutaneous disorders associated with seborrhoea can in particular be acne or greasy skin with a tendency towards acne and/or hyperseborrhoea.

A further subject-matter of the present invention is consequently the use of octoxyglycerol in a cosmetic composition for treating acne and/or greasy skin with a tendency towards acne and/or hyperseborrhoea.

A further subject-matter of the present invention is the use of octoxyglycerol in the manufacture of a medicament intended to treat acne and/or greasy skin with a tendency towards acne and/or hyperseborrhoea.

A further subject-matter of the present invention is the use of octoxyglycerol in a cosmetic composition for acting against microorganisms of the genus Propionibacterium.

A further subject-matter of the present invention is the use of octoxyglycerol in the manufacture of a medicament intended to act against microorganisms of the genus Propionibacterium.

Another subject-matter of the present invention is a process for the cosmetic treatment of seborrhoea and/or of disorders associated with seborrhoea which consists in applying a composition containing at least octoxyglycerol on the skin and/or the scalp exhibiting disorders of seborrhoea.

Another subject-matter of the present invention is a process for the cosmetic treatment of acne, which consists in applying, on skin suffering from acne, a composition containing at least octoxyglycerol.

A final subject-matter of the invention is an anti-acne cosmetic and/or dermatological composition, characterized in that it comprises, in a cosmetically and/or dermatologically acceptable medium, at least an effective amount of octoxyglycerol as anti-acne active agent.

Octoxyglycerol (2-ethylhexyl 1-glyceryl ether) corresponds to the following formula (I):

$$R-O-CH_2-CHOH-CH_2OH \qquad (I)$$

in which R represents a 2-ethylhexyl radical.

Octoxyglycerol is used, according to the present invention, in an amount preferably ranging from 0.05 to 10%, better still from 0.1 to 5% and yet better still from 0.1 to 2.5% of the total weight of the composition.

The compositions according to the invention comprise a cosmetically and/or dermatologically acceptable medium, that is to say compatible with the skin, the mucous membranes, the hair and the scalp. They can be provided in all the pharmaceutical dosage forms appropriate for topical application, in particular in the form of aqueous, aqueous/alcoholic or oily solutions, of aqueous, aqueous/alcoholic or oily gels, of solid or pasty anhydrous products, of emulsions obtained by dispersion of a fatty phase in an aqueous phase (O/W) or vice versa (W/O), of suspensions, of microemulsions, of microcapsules, of microparticles or of vesicular dispersions of ionic type (liposomes) and/or non-ionic type. These compositions are prepared according to the usual methods in the fields under consideration.

The compositions according to the invention can also be used in the form of foams or in the form of aerosol compositions also comprising a pressurized propellent.

The amounts of the various constituents of the compositions according to the invention are those conventionally used in the fields under consideration.

These compositions constitute in particular skin products, such as cleansing or treatment gels or creams, purifying lotions or milks, concealing sticks, anti-seborrhoeic shampoos or hair lotions, or compositions for combating hair loss for the scalp.

The compositions of the invention can comprise the adjuvants conventionally employed in the fields under consideration, such as fatty substances, organic solvents, solubilizing agents, thickening and gelling agents, softeners, antioxidants, opacifying agents, stabilizing agents, foaming agents, fragrances, ionic or non-ionic emulsifiers, fillers, sequestering and chelating agents, preservatives, screening agents, essential oils, dyes, pigments, hydrophilic or lipophilic active agents, lipid vesicles or any other ingredient commonly used in cosmetics. These adjuvants are introduced in the amounts generally used in the cosmetic or dermatological field and, for example, from 0 to 20% of the total weight of the composition.

When the composition of the invention is an emulsion, the proportion of the fatty phase can range from 5 to 80% and preferably from 5 to 50% of the total weight of the composition. The oils, the emulsifiers and the coemulsifiers used in the composition in the emulsion form are chosen from those conventionally used in the cosmetic or dermatological field. The emulsifier and optionally the coemulsifier are present in the composition in a proportion ranging from 0.3 to 30% by weight and preferably from 0.5 to 20% by weight with respect to the total weight of the composition. The emulsion can additionally contain lipid vesicles.

Mention may be made, as oils which can be used in the invention, of mineral oils (isoparaffin), oils of vegetable origin (apricot kernel oil), oils of animal origin, synthetic oils, silicone oils (cyclopentadimethylsiloxane) and fluorinated oils. Use can also be made, as fatty substances, of fatty alcohols, fatty acids (stearic acid) or waxes (carnauba wax, ozocerite).

Mention may be made, as emulsifiers which can be used in the invention, of, for example, ethylene glycol monostearate, sorbitan tristearate, the glycol palmitate-stearate/polyethylene glycol (6 EO) stearate/polyethylene glycol (32 EO) stearate mixture sold under the name "Tefose 63" by the company Gattefosse, and hydrogenated lecithin.

Mention may be made, as gelling or thickening agents, of natural gums (xanthan gum), polysaccharides (hydroxypropylmethylcellulose or carboxymethylcellulose), carboxyvinyl polymers (carbomer), acrylic copolymers, polyacrylamides and in particular the mixture of polyacrylamide, $C_{13}$–$C_{14}$ isoparaffin and Laureth-7 sold under the name of Sepigel 305 by the company Seppic, or oxyethylenated sugar derivatives, such as oxyethylenated methylglucose.

Mention may be made, as foaming agents, of, for example, disodium N-carboxyethoxyethyl-N-(cocoylamidoethyl)aminoacetate, sodium lauryl ether sulphate, sodium lauroyl sarcosinate, triethanolamine lauryl sulphate and the mixture of sodium cocoyl isethionate and of coconut fatty acids.

Mention may in particular be made, as fillers, of acrylic copolymers, such as the ethylene glycol dimethacrylate/lauryl methacrylate copolymer sold by the company Dow Corning under the name of Polytrap.

Mention may in particular be made, as hydrophilic or lipophilic active agents, of agents capable of complementing the effect of the alkyl ether of glycerol in the treatment of seborrhoea and of associated dermatoses and in particular of acne. It can relate, for example, to anti-inflammatory agents, such as benzoyl peroxide, to antibiotics, to antiseptic agents, such as octopirox, to keratolytic agents, such as α-hydroxyacids or β-hydroxyacids in the free, etherified or esterified form, retinoic acid and its derivatives or retinol and its derivatives, such as retinol palmitate, acetate or propionate, or to anti-seborrhoeic agents, such as salts of di- or trivalent metals, such as salts of alkaline earth metals and lanthanides, and more particularly strontium salts and neodymium salts. According to a preferred embodiment of the invention, this agent is a keratolytic agent and in particular a α-hydroxyacid or a β-hydroxyacid.

The amount of agent can range, for example, from 0 to 20% and preferably from 0.05 to 5% of the total weight of the composition.

Mention may in particular be made, as α-hydroxyacids, of glycolic, lactic, malic, tartaric, citric and mandelic acids. Mention may be made, as β-hydroxyacids, of salicylic acid and its derivatives or 2-hydroxyalkanoic acids and their derivatives, such as 2-hydroxy-3-methylbenzoic acid and 2-hydroxy-3-methoxybenzoic acid.

Furthermore, mention may also be made, as hydrophilic active agents, of, for example, proteins or protein hydrolysates, amino acids, polyols (glycerol or propylene glycol), urea, allantoin, sugars and sugar derivatives, vitamins, starch, or bacterial or plant extracts.

When skin suffering from cutaneous disorders related to acne or seborrhoea has to be exposed to the sun, the composition comprising the alkyl ether appropriately comprises, in addition, at least one screening agent, so as to retain the effectiveness of the active agent according to the invention while protecting the skin from the harmful effects of solar radiation. Mention may be made, as screening agents, of organic screening agents or pigments which may or may not be in the form of nanoparticles (nanopigments). Examples of organic screening agents are sulphone or sulphonate derivatives of benzophenone, sulphonic or sulphonate derivatives of benzylidenecamphor, and acrylates, such as octocrylene. The amount of screening agent depends on the solar protection desired. It can range, for example, from 0 to 10% and preferably from 0.1 to 5% of the total weight of the composition.

The following examples illustrate the invention without limiting in any way the scope thereof. The percentages are given by weight.

EXAMPLE 1

Foaming gel for greasy seborrhoeic skin

| | |
|---|---|
| Copolymer of oxyethylenated (60 EO) hydrogenated tallow alcohol/myristyl glycol (solubilizing agent) (Elfacos GT 282 S sold by the company Akzo) | 0.9% |
| Octoxyglycerol | 0.1% |
| Glycerol | 3% |
| Glycolic acid | 1% |
| 38% Disodium N-carboxyethoxyethyl- | 5% |

| | |
|---|---|
| N-(cocoylamidoethyl) aminoacetate in water | |
| Sodium lauryl ether sulphate | 14.3% |
| Diethanolamide of coconut fatty acids (softening agent) | 0.7% |
| Demineralized water q.s. for | 100% |

Procedure:

The Elfacos GT 282S is dispersed in demineralized water at 80° C. and then the dispersion is cooled to 50° C. Furthermore, the foaming agents, the softening agent and the glycerol are dispersed at 50° C. in demineralized water with slow stirring and then this preparation is gently poured, with slow stirring, into the dispersion of Elfacos GT 282S. The octoxyglycerol is subsequently added thereto at 40° C.

The gel obtained is suitable for the treatment of seborrhoeic dermatitis, with application twice daily on the face.

EXAMPLE 2

Foaming cleansing cream for skin suffering from acne

| | |
|---|---|
| Ethylene glycol monostearate | 2% |
| Octoxyglycerol | 2.5% |
| Hydrated magnesium aluminium silicate (stabilizing agent) | 1.7% |
| Hydroxypropylmethylcellulose | 0.8% |
| Mixture of sodium cocoyl isethionate and of coconut fatty acids (Elfan AT 84 G sold by the company Akzo) | 15% |
| Stearic acid | 1.25% |
| 30% Sodium lauroyl sarcosinate in water | 10% |
| Fragrance | 0.3% |
| Demineralized water q.s. for | 100% |

Procedure:

The Elfan AT 84 G is dispersed in demineralized water at 80° C. After complete dissoluton, the hydrated magnesium aluminium silicate salt is added. The mixture is cooled to 60° C. and then the sodium lauroyl sarcosinate and the hydroxypropylmethylcellulose gel are added. The stearic acid and the ethylene glycol monostearate, which have been preheated on a water bath, are subsequently added. The octoxyglycerol and the fragrance are added to this mixture.

The cream obtained is suitable for the treatment of skin suffering from acne, by application twice daily on the face.

EXAMPLE 3

Treatment cream for acne

| | |
|---|---|
| Sorbitan tristearate | 1% |
| Octoxyglycerol | 0.5% |
| Carbomer | 0.4% |
| Xanthan gum | 0.5% |
| Polytrap (Dow Corning) | 1% |
| Cyclopentadimethylsiloxane (volatile oil) | 6% |
| Glycerol | 3% |
| Tefose 63 (Gattefosse) (emulsifier) | 4% |
| Demineraiized water q.s. for | 100% |

Procedure:

The mixture A containing the sorbitan tristearate, the emulsifier and the cyclopentadimethylsiloxane is prepared at 60° C. Furthermore, the mixture B is prepared by swelling, in demineralized water at 70° C., the mixture of glycerol and of carbomer, followed by the xanthan gum. The emulsion is prepared at 65° C. by pouring the mixture A into the mixture B with stirring. The combined mixture is allowed to cool to 50° C. and the Polytrap is added, followed by the octoxyglycerol.

The cream obtained is suitable for the treatment of the skin, by application once daily on the face and the back of the body.

EXAMPLE 4

Treatment gel for seborrhoeic skin

| | |
|---|---|
| Octoxyglycerol | 5% |
| Xanthan gum | 1% |
| Glycerol | 2% |
| Fragrance | 0.2% |
| Ethyl alcohol (solvent) | 30% |
| Oxyethylenated (26 EO)-oxypropylenated (26 PO) butyl alcohol/oxyethylenated (40 EO) hydrogenated castor oil mixture in water (Solubilisant LRI sold by the compant Wacker) (co-solvent) | 1% |
| Demineralized water q.s. for | 100% |

Procedure:

The xanthan gum is swollen in demineralized water with the glycerol at 70° C. After cooling to 30° C., the glycolic acid, the ethyl alcohol, the co-solvent with the octoxyglycerol and the fragrance are added.

The gel obtained is suitable for the treatment of seborrhoeic skin, with application once to twice daily on the face.

EXAMPLE 5

Coloured treatment cream for skin suffering from acne, comprising liposomes

| | |
|---|---|
| Oxyethylenated (5 EO) soybean sterols | 1.6% |
| Hydrogenated lecithin | 2.4% |
| Octoxyglycerol | 2% |
| Apricot kernel oil | 6% |
| Yellow iron oxide (pigments) | 0.45% |
| Brown iron oxides (pigments) | 0.4% |
| Black iron oxide (pigments) | 0.07% |
| Titanium oxide (pigments) | 5% |
| Polytrap (Dow Corning) | 1% |
| Polyacrylamide/$C_{13}$–$C_{14}$ isoparaffin/Laureth-7 (Sepigel 305) | 4% |
| Cyclopentadimethylsiloxane (volatile oil) | 6% |
| Glycerol | 6% |
| Propylene glycol | 6% |
| Demineralized water q.s. for | 100% |

Procedure:

To prepare the liposomes, the mixture of oxyethylenated (5 EO) soybean sterols and of hydrogenated lecithin is hydrated in demineralized water at 80° C. for 2 hours and this preparation is passed twice through a high-pressure homogenizer. After having cooled the liposome preparation to 35° C., the apricot kernel oil and the cyclopentadimethylsiloxane are added thereto. The mixture is passed through the high-pressure homogenizer and cooled to 30° C. Furthermore, a dispersion of the fillers in the propylene glycol and the glycerol is prepared. This dispersion is dispersed in the mixture obtained above. The Sepigel 305 and the octoxyglycerol are subsequently added.

The cream obtained is beige in colour and it is suitable for the treatment of the skin, by application twice daily on the face.

EXAMPLE 6

Concealing stick for greasy skin

| | |
|---|---|
| Octoxyglycerol | 1% |
| Carnauba wax | 8% |
| Ozocerite | 6% |
| Yellow iron oxide (pigments) | 2.5% |
| Brown iron oxides (pigments) | 1% |
| Black iron oxide (pigments) | 0.5% |
| Titanium oxide (pigments) | 20% |
| Polydimethylsiloxane/hydrated silica (mould-release agent) | 0.1% |
| Isoparaffin q.s. for | 100% |

Procedure:

The oxides and the mould-release agent are dispersed in the mixture of waxes and of oil for 2 hours at 100° C. The octoxyglycerol is added thereto immediately before casting.

The stick obtained can be applied on the face several times daily.

EXAMPLE 7

Purifying lotion for skin suffering from acne

| | |
|---|---|
| Octoxyglycerol | 2% |
| Glycerol | 2% |
| Ethyl alcohol (solvent) | 30% |
| Oxyethylenated (26 EO)-oxypropylenated (26 PO) butyl alcohol/oxyethylenated (40 EO) hydrogenated castor oil in water (Solubilisant LRI sold by the company Wacker) (co-solvent) | 1% |
| Demineralized water q.s. for | 100% |

Procedure:

The glycerol, the ethyl alcohol, the cosolvent and the octoxyglycerol are mixed in the demineralized water.

The lotion obtained is suitable for cleansing the skin, by application twice daily on the face.

EXAMPLE 8

Anti-seborrhoeic shampoo

| | |
|---|---|
| Octoxyglycerol | 2% |
| 40% Triethanolamine lauryl sulphate in water | 37% |
| Diethanolamide of coconut fatty acids (hair conditioning agent) | 2% |
| Carboxymethylcellulose | 0.5% |
| Oxyethylenated methylglucose | 2.5% |
| Demineralized water q.s. for | 100% |

Procedure:

The carboxymethylcellulose is dispersed in the demineralized water, and the conditioning agent, the triethanolamine lauryl sulphate and the oxyethylenated methylglucose are added. After having cooled to 40° C., the octoxyglycerol is added.

The shampoo obtained is suitable for washing the hair and makes possible a marked improvement in the condition of the scalp.

Test:

The test described hereinbelow demonstrates the activity of octoxyglycerol with respect to *Propionibacterium acnes* and *Propionibacterium granulosum*.

The stages in carrying out this test are as follows:

1) Culturing the microorganism: *Propionibacterium acnes* and *Propionibacterium granulosum* are cultured on sloping tryptic soy broth agar.
2) Preparation of inoculum: 48 hours before the beginning of the test, the strain is subcultured and incubation is allowed to take place for 48 hours at 35° C. under anaerobiosis conditions. The suspension obtained assays at $10^8$ microorganisms/ml.
3) Preparation of the sample: 32 g of a tryptic soy broth are deposited in a glass bottle, known as a pill bottle, and incubation is allowed to take place at 35° C. for 24 hours. 4 g of the test composition are then added and homogenization is carried out. In parallel, a control is prepared in order to confirm that the microorganisms are under favourable growth conditions throughout the duration of the test.
4) Inoculation: 4 ml of inoculum are introduced into the pill bottle and the pill bottle is placed in the incubator.
5) Removal and counting: after each contact time (2, 4, 6 and 24 hours), the contents of the pill bottle are homogenized and 1 ml is removed therefrom. After having determined the appropriate dilution in order to be able to carry out the counting, this dilution is spread at the surface of agar-comprising Petri dishes (Eugon LT100 medium) and then the Petri dishes are allowed to incubate for 7 days in an oven at 35° C. under anaerobiosis conditions.

The colonies are then counted on the dishes containing more than 20 and less than 200 colonies.

The compositions tested are as follows:

| | Preparation A | Preparation B |
|---|---|---|
| Sterile distilled water | 57.99 g | 59.99 g |
| Propylene glycol | 20 g | 20 g |
| Ethyl alcohol | 20 g | 20 g |
| Lactic acid | 0.01 g | 0.01 |
| Octoxyglycerol | 2 g | — |

The results obtained are shown in the following table. They are expressed as number of microorganisms per gram of preparation:

| | *Propionibacterium acnes* | | *Propionibacterium granulosum* | |
|---|---|---|---|---|
| Contact time | Preparation A | Preparation B | Preparation A | Preparation B |
| 0 | $3.4 \times 10^7$ | $3.4 \times 10^7$ | $3.6 \times 10^7$ | $3.6 \times 10^7$ |
| 2 | $1.7 \times 10^4$ | $6.8 \times 10^7$ | $7.5 \times 10^3$ | $4.5 \times 10^7$ |
| 4 | $5.2 \times 10^9$ | $7.9 \times 10^7$ | <200* | $4.6 \times 10^7$ |
| 6 | $5.2 \times 10^3$ | $9.4 \times 10^7$ | <200* | $4.3 \times 10^7$ |
| 24 | <200* | $1.9 \times 10^8$ | <200* | $3.7 \times 10^8$ |

*Sensitivity threshold of the method

Decontamination is found, from 2 hours of contact, to be greater with Preparation A according to the invention. The number of microorganisms is 1000 times less for *Propionibacterium acnes* and 10,000 times less for *Propionibacterium granulosum* than the inoculation level (T0), whereas, for Preparation B, it is unchanged.

This result is confirmed and accentuated at 24 hours of contact, since the number of revivable microorganisms is below the detection threshold of the method for Preparation A, whereas, in the case of Preparation B, it is approximately ten times greater than the inoculation level (T0).

We claim:

1. A method for treating seborrhoea of the skin and/or of the scalp and/or cutaneous disorders associated with seborrhoea comprising applying to the affected area of a subject in need of said treatment a cosmetic composition comprising an effective amount of octoxyglycerol in a cosmetically acceptable medium therefor.

2. A method of treating seborrhoea of the skin and/or of the scalp and/or cutaneous disorders associated with seborrhoea comprising applying to the affected area of a subject in need of said treatment a medicament comprising an effective amount of octoxyglycerol in a pharmaceutically acceptable medium.

3. A method for treating acne and/or greasy skin which is associated with acne and/or hyperseborrhoea comprising applying to the affected area of a subject in need of said treatment a cosmetic composition comprising an effective amount of octoxyglycerol in a cosmetically acceptable medium.

4. A method for treating acne and/or greasy skin associated with acne and/or hyperseborrhoea comprising applying to the affected area of a subject in need of said treatment a medicament comprising an effective amount of octoxyglycerol in a pharmaceutically acceptable medium.

5. A method for treating a microbial infection associated with microbia of the genus Propionibacterium comprising applying to the infected area of a subject in need of said treatment an effective amount of a medicament comprising a microbial inhibitory effective amount of octoxyglycerol in a pharmaceutically acceptable medium.

6. The method of claim 1, wherein the amount of octoxyglycerol in the cosmetic composition ranges from 0.05 to 10% relative to the total weight of the composition.

7. The method of claim 2, wherein the amount of octoxyglycerol in said medicament ranges from 0.05 to 10% relative to the total weight of the medicament composition.

8. The method of claim 3, wherein the amount of octoxyglycerol in said cosmetic composition ranges from 0.05 to 10% relative to the total weight of the composition.

9. The method of claim 4, wherein the amount of octoxyglycerol in said medicament ranges from 0.05 to 10% relative to the total weight of the medicament composition.

10. The method of claim 5, wherein the amount of octoxyglycerol in said medicament composition ranges from 0.05 to 10% relative to the total weight of the composition.

11. The method of claim 6, wherein the amount of octoxyglycerol ranges from 0.1 to 2.5% relative to the weight of the composition.

12. The method of claim 7, wherein the amount of octoxyglycerol ranges from 0.1 to 2.5% relative to the weight of the composition.

13. The method of claim 8, wherein the amount of octoxyglycerol ranges from 0.1 to 2.5% relative to the weight of the composition.

14. The method of claim 9, wherein the amount of octoxyglycerol ranges from 0.1 to 2.5% relative to the weight of the composition.

15. The method of claim 10, wherein the amount of octoxyglycerol ranges from 0.1 to 2.5% relative to the weight of the composition.

16. The method of claim 1, wherein said composition is in a form selected from the group consisting of aqueous, oil, or aqueous/alcoholic solutions, emulsions, microemulsions, aqueous, oily or anhydrous gels, serums, dispersion of vesicles, and pasty or solid anhydrous products.

17. The method of claim 2, wherein said composition is in a form selected from the group consisting of aqueous, oil, or aqueous/alcoholic solutions, emulsions, microemulsions, aqueous, oily or anhydrous gels, serums, dispersion of vesicles, and pasty or solid anhydrous products.

18. The method of claim 3, wherein said composition is in a form selected from the group consisting of aqueous, oil, or aqueous/alcoholic solutions, emulsions, microemulsions, aqueous, oily or anhydrous gels, serums, dispersion of vesicles, and pasty or solid anhydrous products.

19. The method of claim 4, wherein said composition is in a form selected from the group consisting of aqueous, oil, or aqueous/alcoholic solutions, emulsions, microemulsions, aqueous, oily or anhydrous gels, serums, dispersion of vesicles, and pasty or solid anhydrous products.

20. The method of claim 5, wherein said composition is in a form selected from the group consisting of aqueous, oil, or aqueous/alcoholic solutions, emulsions, microemulsions, aqueous, oily or anhydrous gels, serums, dispersion of vesicles, and pasty or solid anhydrous products.

21. The method of claim 1, wherein said composition is in a form selected from the group consisting of a cream, lotion, gel, and stick.

22. The method of claim 2, wherein said composition is in a form selected from the group consisting of a cream, lotion, gel, and stick.

23. The method of claim 3, wherein said composition is in a form selected from the group consisting of a cream, lotion, gel, and stick.

24. The method of claim 4, wherein said composition is in a form selected from the group consisting of a cream, lotion, gel, and stick.

25. The method of claim 5, wherein said composition is in a form selected from the group consisting of a cream, lotion, gel, and stick.

26. The method of claim 1, wherein said composition comprises at least one adjuvant selected from the group consisting of fatty substances, organic solvents, solubilizing agents, gelling agents, foaming agents, emulsifiers, fillers, screening agents, pigments, hydrophilic or lipophilic active agents, and lipid vesicles.

27. The method of claim 2, wherein said composition comprises at least one adjuvant selected from the group consisting of fatty substances, organic solvents, solubilizing agents, gelling agents, foaming agents, emulsifiers, fillers, screening agents, pigments, hydrophilic or lipophilic active agents, and lipid vesicles.

28. The method of claim 3, wherein said composition comprises at least one adjuvant selected from the group consisting of fatty substances, organic solvents, solubilizing agents, gelling agents, foaming agents, emulsifiers, fillers, screening agents, pigments, hydrophilic or lipophilic active agents, and lipid vesicles.

29. The method of claim 4, wherein said composition comprises at least one adjuvant selected from the group consisting of fatty substances, organic solvents, solubilizing agents, gelling agents, foaming agents, emulsifiers, fillers, screening agents, pigments, hydrophilic or lipophilic active agents, and lipid vesicles.

30. The method of claim 5, wherein said composition comprises at least one adjuvant selected from the group consisting of fatty substances, organic solvents, solubilizing agents, gelling agents, foaming agents, emulsifiers, fillers, screening agents, pigments, hydrophilic or lipophilic active agents, and lipid vesicles.

31. The method of claim 1, wherein said composition further comprises at least one agent selected from the group consisting of α-hydroxyacids, β-hydroxyacids, and salts of di- or trivalent metals.

32. The method of claim 2, wherein said composition further comprises at least one agent selected from the group consisting of α-hydroxyacids, β-hydroxyacids, and salts of di- or trivalent metals.

33. The method of claim 3, wherein said composition further comprises at least one agent selected from the group consisting of α-hydroxyacids, β-hydroxyacids, and salts of di- or trivalent metals.

34. The method of claim 4, wherein said composition further comprises at least one agent selected from the group consisting of α-hydroxyacids, β-hydroxyacids, and salts of di- or trivalent metals.

35. The method of claim 5, wherein said composition further comprises at least one agent selected from the group consisting of α-hydroxyacids, β-hydroxyacids, and salts of di- or trivalent metals.

36. The method of claim 1, wherein said cosmetic composition is topically applied to the skin and/or scalp of a subject exhibiting a seborrhoea disorder.

37. The method of claim 2, wherein said cosmetic composition is topically applied to the skin and/or scalp of a subject exhibiting a seborrhoea disorder.

38. The method of claim 3, wherein said cosmetic composition is topically applied to the skin of a subject comprising acne and/or greasy skin with is associated with acne and/or hyperseborrhoea.

39. The method of claim 4, wherein said medicament is topically applied to the skin of a subject comprising acne and/or greasy skin associated with acne and/or hyperseborrhoea.

* * * * *